United States Patent
Balayan et al.

(10) Patent No.: US 10,221,411 B2
(45) Date of Patent: Mar. 5, 2019

(54) PROCESS FOR MANUFACTURING A COMPOSITE SORBENT MATERIAL FOR CHROMATOGRAPHICAL SEPARATION OF BIOPOLYMERS

(71) Applicants: NExtTec GmbH, Leverkusen (DE); Gurgen Balayan, Yerevan (AM)

(72) Inventors: Hamlet Balayan, Yerevan (AM); Robert-Matthias Leiser, Solingen (DE); Lutz Plobner, Erkrath (DE); Leonti E. Tkachenko, Yerevan (AM); Gottfried Brem, Hilgertshausen (DE)

(73) Assignee: NEXTTEC GMBH, Leverkusen (DE)

( * ) Notice: Subject to any disclaimer, the term of this patent is extended or adjusted under 35 U.S.C. 154(b) by 0 days.

(21) Appl. No.: 15/429,668

(22) Filed: Feb. 10, 2017

(65) Prior Publication Data

US 2017/0152501 A1    Jun. 1, 2017

Related U.S. Application Data

(63) Continuation of application No. 14/966,269, filed on Dec. 11, 2015, now abandoned, which is a continuation of application No. 14/033,074, filed on Sep. 20, 2013, now abandoned, which is a continuation of application No. 12/830,676, filed on Jul. 6, 2010, now abandoned, which is a continuation of application No. 11/547,011, filed as application No. PCT/EP2005/051490 on Apr. 1, 2005, now abandoned.

(30) Foreign Application Priority Data

Apr. 2, 2004   (EP) ..................... 04008147

(51) Int. Cl.
| | |
|---|---|
| *B01J 20/283* | (2006.01) |
| *B01J 20/26* | (2006.01) |
| *B01J 20/10* | (2006.01) |
| *B01J 20/28* | (2006.01) |
| *B01J 20/32* | (2006.01) |
| *B01J 20/289* | (2006.01) |
| *C12N 15/10* | (2006.01) |
| *C08F 212/08* | (2006.01) |
| *C08F 212/14* | (2006.01) |
| *C08F 212/36* | (2006.01) |
| *C08F 292/00* | (2006.01) |
| *C08F 2/44* | (2006.01) |

(52) U.S. Cl.
CPC .......... *C12N 15/101* (2013.01); *B01J 20/103* (2013.01); *B01J 20/261* (2013.01); *B01J 20/265* (2013.01); *B01J 20/283* (2013.01); *B01J 20/289* (2013.01); *B01J 20/28059* (2013.01); *B01J 20/28061* (2013.01); *B01J 20/28083* (2013.01); *B01J 20/28085* (2013.01); *B01J 20/28088* (2013.01); *B01J 20/3204* (2013.01); *B01J 20/3219* (2013.01); *B01J 20/3278* (2013.01); *C08F 212/08* (2013.01); *C08F 212/14* (2013.01); *C08F 292/00* (2013.01)

(58) Field of Classification Search
CPC ..... C12N 15/101; B01J 20/103; B01J 20/261; B01J 20/283
See application file for complete search history.

(56) References Cited

U.S. PATENT DOCUMENTS

| | | | |
|---|---|---|---|
| 4,045,353 | A | 8/1977 | Kosaka et al. |
| 4,600,646 | A | 7/1986 | Stout |
| 4,732,887 | A | 3/1988 | Obanawa et al. |
| 4,891,120 | A | 1/1990 | Sethi et al. |
| 5,163,994 | A | 11/1992 | Klimesch et al. |
| 5,750,258 | A | 5/1998 | Sakai et al. |
| 6,056,877 | A | 5/2000 | Gjerde et al. |
| 6,074,541 | A | 6/2000 | Srinivasan et al. |
| 6,316,527 | B1 | 11/2001 | Meyer |
| 6,417,239 | B1 | 7/2002 | Murray et al. |
| 6,548,264 | B1 | 4/2003 | Tan et al. |
| 6,548,265 | B2 | 4/2003 | Hultgren et al. |

(Continued)

FOREIGN PATENT DOCUMENTS

| | | |
|---|---|---|
| EP | 0441559 A | 8/1991 |
| EP | 1148945 A1 | 10/2001 |

(Continued)

OTHER PUBLICATIONS

CAPlus Abstract of JP 56122815 A.

(Continued)

*Primary Examiner* — Brieann R Johnston
(74) *Attorney, Agent, or Firm* — Keith G. Haddaway; Annette K. Kwok; Venable LLP

(57) ABSTRACT

The present invention relates to a sorbent material for separation and purification of biopolymers, particularly nucleic acids, having a solid support substantially modified with a copolymer coating comprising aromatic monomers and crosslinking compounds and unsaturated esters or ethers preferably attached to the support via a vinylchlorsilane. The use of these materials for separation of nucleic acids, particularly a one-step isolation of DNA from lysates of different biological sources, is an object of the invention as well as a chromatographic column or cartridge at least partially filled with the sorbent material of the invention, a membrane-like device comprising the sorbent material of the invention, and a kit comprising the sorbent material of the invention in bulk or packed in chromatographic devices as well as other devices necessary for performing sample preparations.

18 Claims, No Drawings

(56) References Cited

U.S. PATENT DOCUMENTS

| | | |
|---|---|---|
| 6,824,866 B1 | 11/2004 | Glazer et al. |
| 6,991,852 B2 | 1/2006 | Carr et al. |
| 2003/0134938 A1 | 7/2003 | Nakamura et al. |
| 2004/0209835 A1 | 10/2004 | Kuhne |

FOREIGN PATENT DOCUMENTS

| | | |
|---|---|---|
| JP | 56122815 A | 9/1981 |
| JP | 05-170802 | 7/1993 |
| JP | 2002194025 A | 7/2002 |
| WO | WO-9907754 A1 | 2/1999 |
| WO | WO-2004041428 A2 | 5/2004 |

OTHER PUBLICATIONS

Derwent Abstract of JP 56122815 A.
Derwent Accession No. 2003-123100.
Japanese Abstract of JP 56122815 A.
Prepartion of Naval Macroporous Silica-Based Amide-Polymer-Bonded Packing and Its Application to the Separation of Proteins. Analytical Letters, 31, 9, 1487-1497, 1998.

PROCESS FOR MANUFACTURING A COMPOSITE SORBENT MATERIAL FOR CHROMATOGRAPHICAL SEPARATION OF BIOPOLYMERS

This application is a continuation of U.S. patent application Ser. No. 14/966,269, filed Dec. 11, 2015, which is a continuation of U.S. patent application Ser. No. 14/033,074, filed Sep. 20, 2013, which is a continuation of U.S. patent application Ser. No. 12/830,676, filed Jul. 6, 2010, which is a continuation of U.S. patent application Ser. No. 14/547,011, filed Oct. 2, 2006, which is a National Stage of PCT/EP2005/051490, filed Apr. 1, 2005, which claims priority to EP Application No. 04008147.3, filed Apr. 2, 2004, each of which is hereby incorporated by reference.

The present invention relates to a sorbent material for separation and purification of biopolymers, particularly nucleic adds, having a solid support substantially modified with a copolymer coating comprising aromatic monomers and crosslinking compounds and unsaturated esters or ethers preferably attached to the support via a vinylchlorsilane. The use of these materials for separation of nucleic adds, particularly a one-step isolation of DNA from lysates of different biological sources, is an object of the invention as well as a chromatographic column or cartridge at least partially filled with the sorbent material of the invention, a membrane-like device comprising the sorbent material of the invention, and a kit comprising the sorbent material of the invention in bulk or packed in chromatographic devices as well as other devices necessary for performing sample preparations.

The development of composite sorbent materials for stationary phases has led to substances with a wide range of chromatographic properties. These materials with modified surfaces are widely used in separation processes. Mostly, a hydrophilic support material, such as silica gel, is modified with hydrophobic moieties like alkyl chains of different length.

Many efforts have been made to improve the properties of the chromatographic material in terms of chemical stability, the field of applications or selectivity. Modification of the surface material moderates the properties of the stationary phases and influences the separation which is based on hydrophilic, hydrophobic or ion-ion interactions.

U.S. Pat. No. 4,045,353 describes a chromatographic material prepared by radiation of polymerisable monomers absorbed on a microporous inorganic substrate. The sorbent material thus obtained is suitable for separation of relatively small molecules, but there is insufficient selectivity for separation of biopolymers like nucleic acids.

Efforts have been made to get composite fluorinated materials, in particular sorbents manufactured on the basis of solid porous silica gels. This is to combine in the same material the mechanical strength, determined by the porous nature of the inorganic matrix and the specific sorption properties of the fluorinated polymeric modifying compound. EP 1 148 945 discloses a material having a solid support of controlled pore glass and a coating of crosslinkable olefinic oligomers. Fluorination of the oligomer coated support is effected with gaseous xenon difluoride ($XeF_2$), optionally under inert gas conditions, or with a mixture of fluorine and an inert carrier gas. The composite material thus obtained is suitable for use in the isolation of DNA out of complex mixtures, where apart of DNA also RNA, proteins, low molecular substances and salts are present. But, because of the exclusively hydrophobic nature of these materials, there are certain difficulties in using them with aqueous solutions of biopolymers and they are much more used for chromatographic separations in columns with increased pressure (HPLC) and operations using hydrophobic interaction chromatography (HIC). Moreover, preparation of these materials is somewhat complicated, laborious and ecologically harmful.

Another suggestion was made to prepare sorbents on the basis of macroporous silica gels, modified with vinyl monomers like N-vinyl-pyrrolidone, styrene, ethylene, vinylethyl ether (authors certificate, USSR, No. 687081, 1979). The sorbent materials are manufactured in applying said monomers to γ-aminopropylated or silanised silica gel and subsequent polymerisation. These sorbents possess good mechanical stability, do not swell in solvents and may be used for the separation of proteins and other active biomolecules. No hint is given for using these materials in the separation of nucleic acids.

The enormous progress in genetic engineering connected with PCR-technology leads to a growing need for applications which lead to the desired products in a fast and economic way, e.g. isolation and purification of DNA with effective removal of by-products and impurities providing the capacity for the isolation of biopolymers without denaturating conditions, and improving the selectivity by modifying the surface of the coating.

Therefore, the object of the present invention is to provide a sorbent material with improved characteristics in separation and purification capacity and increased selectivity in the specific action of the sorbent material on biopolymers having an advanced surface for biotechnological applications, such as isolation and separation of biopolymers, primarily in aqueous media, with improved access area of the separation surface in a separation medium and improved stability of the coating for the construction of material suitable for chromatographical applications like HPLC and fast sample preparations via solid phase extraction in compact cartridges for PCR-applications.

The object is solved by a polymer obtainable by a process of polymerizing at least three components [A], [B], and [M] wherein
   [A] is at least one aromatic or aliphatic compound having at least one polymerisable unsaturated moiety,
   [B] is at least one cross-linkable aromatic or aliphatic compound, and
   [M] is an organic non-saturated polymerisable compound different from [A] having hetero atoms in the C—C chain or in side chains wherein the process comprises the steps of
      admixing the components [A], [B], and [M] sequentially or non-sequentially,
      polymerising the resulting mixture composition
      removing unreacted material and
      recovering and drying the composite material.

In one embodiment the polymer of the invention comprises the following structure

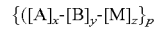

wherein [A], [B], and [M] have the same meaning as in claim 1 and x, y, and z are independent of each other an integer of 1-100 and p is a number between 2 and 5000.

Subject matter of the invention is also a monomer having the structure $[A]_x\text{-}[B]_y\text{-}[M]_z$ wherein [A], [B], and [M] have the same meaning as in claim 1 and x, y, and z is independent of each other an integer of 1-100

A chromatographic material comprising essentially a polymer of the invention is also subject matter of the invention as well as a composite sorbent material having a support which is at least partially covered by a polymer coating of the invention.

According to the invention, a sorbent material is provided having a previously dehydrated solid support having a copolymer coating comprising substituted or unsubstituted aromatic vinyl monomers, substituted or unsubstituted aromatic crosslinking compounds and optionally non-saturated carboxylic acids or esters or non-saturated alcohols or ethers, respectively. The coating can be attached to the support via a vinylchlorsilane. Substituents of the compounds of the copolymer coating modify the hydrophobic/hydrophilic properties on the surface of the coating and provide an essentially improved selectivity for selected applications. For example, the functional groups exhibiting hydrophilic properties provide an essentially better wetting of the inner and outer surfaces of the pores of the sorbent material.

Preferably the support of the sorbent material of the invention is porous inorganic material selected from the group comprising inorganic metal oxides, such as oxides of aluminum, titanium, zirconium, silicon and/or iron. In particular preferred is silica gel having an average pore size of 100-2000 Å, preferably 300-1000 Å, and a specific surface of 20-300 m$^2$/g, more preferably 20-200 m$^2$/g or 20-100 m$^2$/g.

Preferably, the support containing inorganic materials is in particle-like or monolithic membrane-like form and has a porous structure which shows a bidisperse or oligodisperse distribution of pore sizes. Such structures build, e.g., the basis for sorbent materials according to the present invention, which allow additionally to the separation of biopolymers such as nucleic acids the improved retention of low molecular weight substances having, e.g., molecular weights of less than 500 Da, salts and proteins, whereas nucleic acids are passing without retention. In a preferred embodiment, the separation of nucleic acids, e.g. DNA, is conducted in one step. Such bidisperse supports may preferentially be obtained by means of gelling (gel building) of silica sots, starting the process with the mixture of two size types of monodisperse colloidal silica particles. The mass proportion of these two types of colloidal particles determines the proportion and distribution of differently sized pores in the final silica support material.

Typically, two types of silica sols are prestructured prior to mixing. Prestructuring occurs, e.g., by temperature treatment or other methods and partially evaporating water. Preferably, the ratio of the mean diameter of the large pore size distribution and the lower pore size distribution is in the range of 2-15 or 3-15 nm, in particular 4-10 nm. Preferably, the mean diameter of the larger pore size distribution should not be smaller than 25 to 50 nm and should not exceed 200 nm (2000 Å), preferably 100 nm (1000 Å). Especially preferred mean diameters of the large pore size distribution are in the range of 20-100, more preferably 25-80 nm. The mass proportion of the smaller to larger pores represents (90-60, preferably 85-70); (10-40, preferably 15-30) (in %).

The polymer coating preferably has a thickness of about 10 to 250 Angström, preferably 10 to 100 Angström and micropores of less than 50 Å accessible to water, salts, and low molecular weight substances being non-adsorptive towards nucleic acids and adsorptive towards proteins.

The preparation of the composite sorbent material which is at least partially covered by a copolymer coating according to the general formula (with dimethylvinylchlorosilane exemplary chosen as modifying agent)

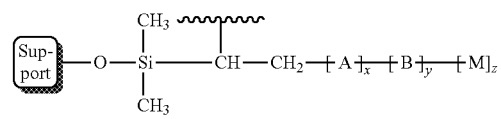

is characterised by the following process.

The previously dried support material is modified by treating it with a boiling solution of a vinylchlorsilane. Treatment of the surface of the support material is conducted at boiling temperature of the solvent used. This treatment enables the following chemosorption of the copolymer and is the basis for enhanced chemical stability and durability of the final sorbent material. Washing of the silanised support, e.g. silica gel, for removal of unreacted silane is done by multiple extraction with organic solvents (ethanol, acetone, toluene, dioxane).

This is followed by addition of a) at least one unsubstituted or substituted styrene or vinylnaphthalene [A] of general formula

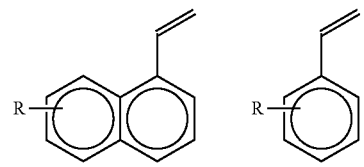

R=H; 2, 3, 4-OH; —COOH; —NO$_2$; —Cl; —Br; —F; —OAlk; —OAc; —NH$_2$; —NHAc; —N(Alk)$_2$; -Alk (C$_1$-C$_{15}$)

which may be substituted by at least one hydroxyl-, carboxy-, nitro-, chloro-, bromo-, fluoro-, alkoxy-, acetoxy-, amino-, mono- or dialkylamino-, acetamino-, alkyl(C$_1$-C$_{15}$)-group, b) at least one cross-linkable unsubstituted or substituted (1,4 or 1,2)-divinylbenzene [B] of general formula

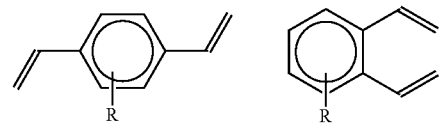

R=H; 2, 3, —OH; —COOH; —NO$_2$; —Cl; —Br; —F; —OAlk; —OAc; —NH$_2$; —NHAc; —N(Alk)$_2$; -Alk (C$_1$-C$_{15}$)

which may be substituted by at least one hydroxyl-, carboxy-, nitro-, chloro-, bromo-, fluoro-, alkoxy-, acetoxy-, amino-, mono- or dialkylamino-, acetamino-, alkyl(C$_1$-C$_{15}$)-group, c) optionally a non-substituted carboxylic acid or alkyl, aryl, or hydroxylalkyl ester thereof [M] of general formula

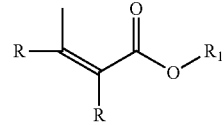

R$_1$=H; Ar; Alk.(C$_1$-C$_{12}$); —(CH$_2$—)$_n$OH n=2-18 R=H; Ar; Alk (C$_1$-C$_{12}$)

respectively a non-saturated alcohol or ether of general formula

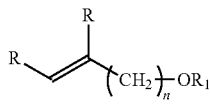

n=1-18
R=H; Ar; Alk.($C_1$-$C_{12}$)
$R_1$=H; Ar; Alk.($C_1$-$C_{12}$); -(-$CH_2$-)$_m$OH m=2-18

In a preferred embodiment, the mass ratio of copolymer components [A], [B], and [M] compiles with the formula [A]:[B]:[M]=1:0.03-0.30:0-0.2.

Polymerisation of the copolymer composition is performed by polymerisation in solution of an organic solvent for a period of 2 to 8 h at the boiling temperature of the solvent or in aqueous solution (emulsion polymerisation) with an emulgator and in the presence of an initiator for radical polymerisation. Suitable initiators comprise benzoyl peroxide, potassium peroxodisulfate as a water soluble initiator, ammonium persulfate, etc. Preferably, a 5-20% solution of copolymer is used. A mass ratio of silica gel matrix and solution of 1:3-6 is also preferred. Finally unreacted material is removed and the composite material is recovered and dried.

The sorbent material according to the invention is useful in separation processes, enhancing the ease of handling and the speed of these processes. Preferably, the substances to be separated are nucleic acids and/or proteins. A conventionally used chromatographic column or cartridge can be filled, at least partially, with the sorbent material of the invention. The sorbent material of the invention behaves similar to other solid chromatographic supports so that the methods for filling chromatographic columns or cartridges can be used in an analogous manner. The support for carrying out chromatographic separations can also be provided in the form of a membrane-like item comprising the sorbent material of the invention, wherein the sorbent material is embedded in a polymeric matrix such as a nylon membrane. Also other membrane materials which are used in preparation, isolation or separation of biomolecules can be used as matrix for embedding a sorbent material of the present invention.

In order to ease the use of a chromatographic material of the invention it is advantageous to provide the sorbent material according to the invention in bulk or a chromatographic column or cartridge or membrane-like device together with filter materials, reagents and/or buffers or other devices or chemicals for performing fast sample preparations and chromatographic separations. This item can especially be provided in form of a kit or a miniaturized device in form of chips or microreactors. The chromatographic separation is not limited in its scale. It can be used in any chromatographic operation for separation, isolation, identification, purification and/or detection of biomolecules, in particular nucleic acids, in preparative or analytical scale.

The present invention provides a product with advanced sorption properties that allows to use this product for chromatography of biopolymers according to the object of the invention. The process of the invention leads to a sorbent material with high binding capacity towards proteins and minimal non-specific sorption of nucleic acids, which is accomplished by using copolymers having complementary functional groups. The inventive process allows manufacturing of a sorbent with adjusted hydrophilic properties having high mechanical stability and very good hydrodynamic characteristics.

The invention is further explained in the following examples which are understood to be not limiting.

EXAMPLE 1

10 g of macroporous silica gel previously dried in vacuo at 200° C. for 3 h having an average pore diameter of 500 Å are treated with a boiling 5% solution of dimethylvinylchlorosilane in dry benzene (3×25 ml) followed by acetone (3×25 ml) and finally with distilled water (5×20 ml), air dried for 1 h at 20° C. and further for 2 h at 120° C. in vacuo. The thus obtained hydrophobic silica gel is suspended in 50 ml of water containing 0.7 g of an emulgator (sodium stearate). Thereafter 2.6 ml styrene, 0.32 ml divinylbenzene, 0.30 ml 2-hydroxyethyl methacrylate and 0.017 g potassium peroxodisulfate as polymerisation initiator are added. The polymerisation is conducted for 4 h at 85° C. The liquid phase is separated by decanting and the sorbent is washed with dimethylformamide as long as the refractive index of the washing no longer differs from that of the solvent (ca. 60 ml). Subsequently washing is continued with 3×25 ml of ethanol and distilled water, respectively. Finally, the sorbent material is dried in vacuo for 3 h at 80° C.

EXAMPLE 2

The sorbent has been obtained similar to example 1, but with a polymer composition without component [M] (2-hydroxyethylmethacrylate).

EXAMPLE 3

10 g of macroporous silica gel having an average pore diameter of 1000 Å is treated with a 3% solution of dimethylvinylchlorosilane according to example 1. Thereafter the thus obtained silanised silica gel is transferred into a three-necked bulb equipped with a stirrer, a thermometer, and a reflux condenser. The bulb is charged with 30 ml benzene, 2.9 ml vinylphenol, 0.50 ml divinylbenzene, 0.16 ml methacrylic acid, and 0.33 ml benzoyl peroxide. The polymerisation is conducted for 4 h at 80° C. Further treatment is carried out according to example 1.

EXAMPLE 4

The sorbent has been obtained similar to example 3, but with a polymer composition without component [M] (methacrylic acid).

EXAMPLE 5

10 g of macroporous silica gel previously dried in vacuo at 200° C. for 3 h having an average pore diameter of 300 A are treated with a boiling solution of dimethylvinylchlorosilane corresponding to example 1. The thus obtained silanized silica will be transferred into a three bottlenecked flask with a stirrer, a thermometer and a reflux condenser. To the flask 40 ml toluene, 3 ml chlorovinyl benzene, 0.4 ml divinylbenzene, 0.4 ml allylic alcohol and 0.30 g benzoil peroxide will be added. The polymerization is conducted for 6 h at 102° C. The further treatment will be achieved corresponding to example 1.

EXAMPLE 6

The sorbent has been obtained similar to example 5, but with a polymer composition without component [M] (allylic alcohol).

The results of usage the obtained sorbents according to examples 1 to 6 for the separation of DNA from proteins and low molecular weight compounds corresponding to the protocol for lysis and isolation of genomic DNA from bacteria in example 9 and the protocols for the estimation of protein retention, retention of salt and yield estimation for DNA, given in example 9 as well.

TABLE

Comparison of separation efficiencies by using sorbent of Examples 1 to 6 underlining the importance of introducing component [M] into the separation of polymer coating

| Support | Chemical composition of polymeric layers | Protein retention (% of 750 BSA) | Salt retention (% of 1M $CuSO_4$) | DNA recovery (% of applied E. coli lysate) |
|---|---|---|---|---|
| Silianized $SiO_2$ | 1. Styrene-divinylbenzene-hydroxyethyl-methacrylate (1:0.12:0.13) | 99.5 | 72.7 | 45.0 |
| | 2. Styrene-7 divinylbenzene (1:0,0.12) | 67.0 | 59.5 | 29.2 |
| Silianized $SiO_2$ | 3.2-Hydroxyvinyl-benzene-divinyl-benzene-methacrylic acid (1:0.16:0.06) | 98.9 | 73.2 | 43.8 |
| | 4:2-Hydroxyvinyl-benzene-divinyl-benzene (1:0.16) | 65.5 | 51.5 | 22.2 |
| Silianized $SiO_2$ | 5. Chlorovinyl-benzene-divinyl-benzene-allylalcohol (1:0.10:0.10) | 99.0 | 73.0 | 44.5 |
| | 6. Chlorovinyl-benzene-divinyl-benzene (1:0.1) | 62.7 | 49.0 | 23.8 |

EXAMPLE 7

For the synthesis of sorbents having a silica gel support with controlled bidisperse pore structures preparation is conducted as follows:

The two starting types of silica sol in water had following characteristics:

A: particle diameter: 6 nm; $SiO_2$ concentration: 22 mass %; $Na^+$-stabilised pH: 9.1

B: particle diameter: 40 nm; $SiO_2$ concentration: 40 mass %; $Na^+$-stabilised pH: 9.2

Water from the two silica sols was evaporated at pH 5.0 in a water bath at 80° C. by constant stirring until 30 and 60 mass %, respectively. To 100 ml of sol A structured by evaporation were added 50 ml of structured sol B and the evaporation has been continued until the formation of a homogeneous gel. The silica hydrogel obtained after 4 hours sinerethis (partial shrinkage) was dried, first for 4 hours at 80° C. in a water bath, followed by 3 hours at 130° C. in a drying hood. Afterwards the product was treated at 600° C. for 5 hours in a muffel oven. The ready obtained silica gel was grinded, fractionated and analysed for pore size distribution both by mercury porometry (according to DIN 66 133 (1993)) and BET-method (according to ISO 9277). These analyses showed a preferential pore size in two classes of 5 nm (appr. 85%) and 28 nm (appr. 15%) and a sorption volume of 0.7 $cm^3$/g.

EXAMPLE 8

The two starting types of silica sol in water had following characteristics:

A: particle diameter: 10 nm; $SiO_2$ concentration: 30 mass %; $Na^+$-stabilised pH: 9.2

B. particle diameter: 80 nm; $SiO_2$ concentration: 50 mass %; $Na^+$-stabilised pH: 9.1

The silica gel sorbent was prepared as in example 7, with following variations:

Water from the two silica sols was evaporated at pH 4.5 in a water bath at 80° C. by constant stirring until 52 and 60 mass %, respectively. To 100 ml of sol A structured by evaporation were added 130 ml of structured sol B. Analyses showed a preferential pore size in two classes of 7 nm (appr. 75%) and 60 nm (appr. 25%) and a sorption volume of 0.75 $cm^3$/g.

The results of usage the obtained sorbents according to examples 1 to 6 for the separation of DNA from proteins and low molecular weight compounds corresponding to the protocol for lysis and isolation of genomic DNA from bacteria in example 9 and the protocols for the estimation of protein retention, retention of salt and yield estimation for DNA, given in example 9 as well.

EXAMPLE 9

Testing of the Sorbents

Mercury Porometry

The porogrammes obtained by testing the sorbents based on the macroporous silica gel show the distribution of the pores in differential and integral manner and allow to determine the medium pore size of the sorbent as well as the effective thickness of the polymeric layer, which is 5-7.5 nm.

Protocol for Tissue Lysis and Extraction of Genomic DNA from Tissue Samples in a Kit Comprising the Sorbent of the Invention The kit contains all necessary reagents for lysis of cells or tissue and genomic DNA purification. The resulting DNA is suitable for most enzymatic reactions (restriction digests, PCR, sequencing etc.).

Compared to most other protocols not DNA is retained by the column resin, but proteins, detergents and low molecular weight compounds are. DNA flows through the column during a short, one-step purification procedure.

Storage Conditions

All kit components are stable at room temperature during shipment. After arrival store the kit at +2° C. to +8° C. Columns may be stored at room temperature.

Materials

| | |
|---|---|
| Buffer G1 | 10 vials (blue), each for 5 isolations |
| Buffer G2 | 10 vials (blue), each for 5 isolations |
| Nexttec clean-columns | 50 columns |

Materials Not Provided

Eppendorf tubes (1.5 ml)
Tris-HCl, 50 mM, pH 8

Preparation of Buffers

1. Immediately before use add 1.6 ml of deionized water to a tube with lyophilised buffer G1. Dissolve the constituents by vortexing the tube.
2. Shortly centrifuge a tube containing buffer G2 to collect the components at the bottom of the tube.
3. Transfer the solution of buffer G1 completely to one aliquot (tube) of buffer G2
4. Mix the buffers to get a homogeneous solution.
5. The mixture contains all components necessary for tissue or cell lysis and is now ready for use. The mixture is sufficient for 5 isolations. (The mixture should be used immediately. Therefore, prepare only as much buffer as needed for the number of samples to be analysed.)

Cell or Tissue Lysis 1. transfer cells or a tissue sample into an Eppendorf tube (<15 mg fresh weight)
2. add 300 µl of lysis buffer mixture (see preparation of buffers) to each cell or tissue sample
3. incubate the samples at 60° C. overnight with constant shaking at ~800 rpm in an Eppendorf thermomixer. (If fresh tissue is used, shorter incubation periods may be sufficient for complete lysis).
4. clear the lysate by centrifugation for 3 min at 20,000×g
5. Take 120 µl from the dear supernatant for DNA purification. The remaining lysate can be stored at −20° C.

Purification of DNA 6. open the spin-columns, add 300 µl Tris-HCl buffer (50 mM, pH 8.0) onto each column. (The buffer enters the resin.)
7. centrifuge the columns at 350×g (corresponds to approx. 2,000 rpm in a 24-place Eppendorf rotor of a microfuge) for 1 min to remove excess of buffer
8. discard the collection tubes with the buffer, place the columns into a new Eppendorf tube and open the columns
9. transfer 120 µl of the cleared supernatant from step 4 onto the columns and close the lids (the lysate enters the resin layer)
10. Incubate the columns for 3 min at room temperature
11. spin the tubes with the columns at 700×g (corresponds to approx. 3,000 rpm in a 24-place Eppendorf rotor of a microfuge) for 1 min
12. The flow-through contains the purified DNA. Discard the columns and use the DNA immediately or store it at −20° C.

Protocol for Lysis and Isolation of Genomic DNA from Bacteria Using a Kit of the Invention The kit contains all necessary reagents for lysis of bacterial cells and DNA purification. It is approved for many Gram(−) as well as Gram(+) bacteria. The resulting DNA is suitable for most enzymatic reactions (restriction digests, PCR, sequencing etc.).

Compared to most other protocols not DNA is retained by the column resin, but proteins, detergents and low molecular weight compounds are. DNA flows through the column during a short, one-step purification procedure.

Storage Conditions

All kit components are stable at room temperature during shipment. After arrival store RNase solution at −20° C. The other kit components must be stored at +2° C. to +8° C. Nexttec clean-columns may be stored at room temperature.

Materials Provided

| | |
|---|---|
| Buffer B1 (basis buffer) | 5 vials (white), each for 10 isolations |
| Buffer B2 | 5 vials (white), each for 10 isolations |
| Buffer B3 | 5 vials (white), each for 10 isolations |
| Nexttec clean-columns | 50 columns |
| RNase solution | 1 vial (white), for 50 isolations |

Materials Not Provided

Lysozyme
Eppendorf tubes (1.5 ml)
Tris-HCl, 50 mM, pH 8

Preparation of Buffers

6. Prepare a 25 mg/ml lysozyme solution in pure water (use lyophilized lysozyme for example from Sigma Kat.-Nr. L-6876 or comparable). The dissolved lysozyme should be stored frozen at −20° C.
7. Each vial with buffer B1 (basis buffer) is sufficient for 10 DNA preparations. Immediately before use complete the buffer by adding 110 µl lysozyme stock solution (20 mg/ml) and 220 µl RNase solution. Mix by vortexing the tube.
8. Shortly centrifuge a vial containing buffer B2 to collect the components at the bottom of the tube, then add 550 µl deionized water and vortex. The prepared buffer B2 can be stored for 2 days at +4° C.
9. Add 550 µl deionized water to one vial with buffer B3 and dissolve the constituents by vortexing. The resuspended buffer should be used immediately.

Lysis of Bacterial Cells 1. grow an overnight culture of bacteria in a suitable medium (e.g. LB, CSB)
2. transfer 0.5 ml of the culture to 1.5 ml Eppendorf tubes (1.5 $OD_{600}$)
3. pellet the cells by centrifugation at 6,000×g for 1 min, remove and discard the supernatant
4. add 120 µl buffer B1 (containing lysozyme and RNase solution) to the bacterial cell pellet
5. gently vortex the tube to resuspend the cells
6. Incubate the tube for 10 min at 60° C. constantly shaking (1,200 rpm, Eppendorf thermomixer)
7. add 50 µl of buffer B2 and incubate for 5 min at 60° C. (1,200 rpm, Eppendorf thermomixer)
8. then add 50 µl of buffer B3 and continue the incubation at 60° C. for 25 min (as described in step 7) in the thermomixer 9. In most cases the lysate should be clear after the incubation. If it is not, centrifuge the tube for 3 min at 20,000×g to pellet cell debris.

Purification of DNA 10. open the spin-columns, add 300 μl Tris-HCl buffer (50 mM, pH 8.0) onto the column. (The buffer enters the resin.)

11. centrifuge the columns at 350×g (corresponds to approx. 2,000 rpm in a 24-place Eppendorf rotor of a microfuge) for 1 min to remove excess of buffer 12. discard the collection tubes with the buffer, place the columns into new Eppendorf tubes and open the columns 13. transfer 120 μl of the dear lysate from step 9 onto the columns and close the lid (the lysate enters the sorbent layer)

14. incubate the columns for 3 min at room temperature 15. centrifuge the tubes with the columns at 700×g (corresponds to approx. 3,000 rpm in a 24-place Eppendorf rotor of a microfuge) for 1 min 16. The flow-through contains the purified DNA. Discard the columns and use the DNA immediately or store it at −20° C.

Protein retention was measured using bovine serum albumin (BSA) as a model protein. BSA was dissolved in buffer and the optical density of the resulting solution at a wavelength of 280 nm was measured before and after passing columns containing different sorbents. The concentration of BSA in both solutions was then calculated using a linear regression resulting from a standard curve of different BSA concentrations in buffer. The applied amount of BSA was set at 100% and the eluted amount of BSA was recalculated in % of the applied amount. The difference between both values gives a protein retention in %.

Salt retention was measured using copper sulphate ($CuSO_4$) as a model salt. A solution of this salt in water results in a blue coloured liquid. The optical density of the solution is linearly depending on the $CuSO_4$ concentration. $CuSO_4$ was dissolved in water (c=1M) and the optical density of the resulting solution at a wavelength of 650 nm was measured before and after passing columns containing different sorbents. The concentration of $CuSO_4$ in both solutions was then calculated using a linear regression resulting from a standard curve of different $CuSO_4$ concentrations in water. The applied amount of $CuSO_4$ was set at 100% and the eluted amount of $CuSO_4$ was recalculated in % of the applied amount. The difference between both values gives the salt retention in %.

To determine the DNA recovery for sorbents during passage of columns filled with corresponding chromatographic materials a crude lysate from *Escherichia coli* cells was obtained. The lysate contains low molecular weight compounds, proteins (peptides), nucleic acids and other compounds.

The concentration of DNA before (crude lysate) and after (eluate) passing a sorbent containing column was measured using PicoGreen, a fluorescent dye, which binds only to doublestranded DNA, according to the manufacturer's instructions (Molecular Probes c/o Invitrogen). For the preparation of a standard curve a serial dilution of DNA from the bacteriophage lambda with known concentration was used. The applied amount of DNA within the lysate was set at 100% and the eluted amount of DNA was recalculated in % of the applied amount. The resulting value gives the DNA recovery in %.

The invention claimed is:

1. A process for the purification and/or isolation of nucleic acids wherein the process comprises lysing cells yielding a sample containing nucleic acids and proteins, contacting the sample with a sorbent material binding the proteins, and collecting the eluate containing the nucleic acids, where the sorbent material comprises a porous inorganic material comprising silica which is at least partially covered by a polymer coating having the general formula

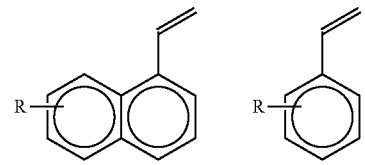

wherein the mass ratio of copolymer components [A], [B], and [M] complies with the formula 1:0.03-0.3:0-0.2 and

[A] is derived from a monomer with general formula

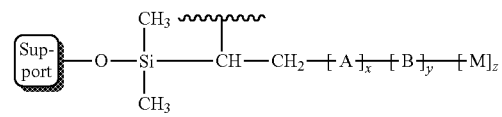

R = H; 2, 3, 4 —OH; —COOH; —$NO_2$; —Cl; —Br; —F; —OAlk; —OAc; —$NH_2$; —NHAc; —$N(Alk)_2$; —Alk($C_1$–$C_{16}$);

[B] is derived from a monomer of general formula

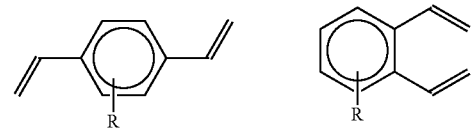

R = H; 2, 3, —OH; —COOH; —$NO_2$; —Cl; —Br; —F; —OAlk; —OAc; —$NH_2$; —NHAc; —$N(Alk)_2$; —Alk($C_1$–$C_{16}$);

and

[M] is derived from a monomer of general formula

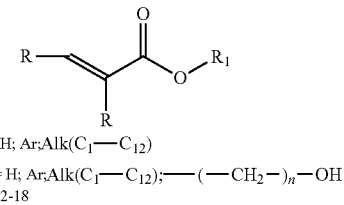

R = H; Ar;Alk($C_1$—$C_{12}$)
$R_1$ = H; Ar;Alk($C_1$—$C_{12}$); —(—$CH_2$—)$_n$—OH
n = 2-18 or a monomer of general formula

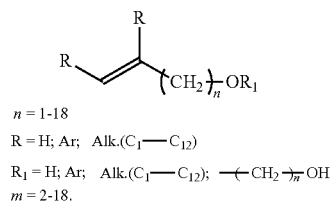

$n = 1\text{-}18$
$R = H; Ar; Alk.(C_1\text{---}C_{12})$
$R_1 = H; Ar; Alk.(C_1\text{---}C_{12}); \text{---}(CH_2)_{\overline{m}}OH$
$m = 2\text{-}18.$ wherein the sorbent material has a high binding capacity towards proteins and minimal non-specific sorption of nucleic acid.

2. The process of claim 1 wherein the support is a porous inorganic material further comprises inorganic metal oxide.

3. The process of claim 2 wherein the porous inorganic metal oxides show a bidisperse distribution of pore sizes.

4. The process of claim 1 wherein the porous inorganic material has an average pore size of 2-200 nm.

5. The process of claim 1 wherein the polymer coating has a thickness of about 10 to 250 Angstrom.

6. The process of claim 2 wherein the inorganic metal oxide is selected from the group consisting of oxides of aluminum, titanium, zirconium, iron oxides, controlled pore glass (CPG), diatomaceous earth and combinations thereof.

7. The process of claim 3 wherein the porous inorganic metal oxide shows a bidisperse distribution with mean pore diameters in the range of 20-100 nm for the larger pore size.

8. The process of claim 7 wherein the porous inorganic metal oxide has a mean pore diameter in the range of 2-15 nm for the smaller pore size.

9. The process of claim 7 wherein the ratio of the mean diameter of the large pore size distribution and the lower pore size distribution is in the range of 2-15.

10. The process of claim 4, wherein the porous inorganic material has an average pore size of 2-100 nm.

11. The process of claim 4 wherein the porous inorganic material has a specific surface area of 20-300 m$^2$/g.

12. The process of claim 11 wherein the porous inorganic material has a specific surface area of 20-100 m$^2$/g.

13. The process of claim 5 wherein the polymer coating has a thickness of 10 to 100 Angstrom.

14. The process of claim 5 wherein the polymer coating has micropores of less than 50 Angstrom accessible to water, salts, and low molecular weight substances.

15. The process of claim 5 wherein the polymer coating is non-adsorptive towards nucleic acids and adsorptive towards proteins.

16. The process of claim 1 comprising component [M].

17. The process of claim 16, wherein [M] is selected from the group consisting of hydroxyethyl methacrylate, methacrylic acid and allyl alcohol.

18. The process of claim 1, wherein x and y are independent of each other, x and y are an integer of 1-100 and z is an integer of 0-100.

* * * * *

UNITED STATES PATENT AND TRADEMARK OFFICE
CERTIFICATE OF CORRECTION

PATENT NO. : 10,221,411 B2
APPLICATION NO. : 15/429668
DATED : March 5, 2019
INVENTOR(S) : Balayan et al.

Page 1 of 1

It is certified that error appears in the above-identified patent and that said Letters Patent is hereby corrected as shown below:

On the Title Page

In the Applicants Item (71), replace "NExtTec GmbH, Leverkusen (DE); Gurgen Balayan, Yerevan (AM)" with -- NExtTec GmbH, Leverkusen (DE) --

In the Specification

In Column 1, beginning on Line 11, replace "a continuation of U.S. patent application Ser. No. 14/547,011, filed Oct. 2, 2006, which is a National Stage of PCT/EP2005/051490, filed Apr. 1, 2005, which claims priority to EP Application No. 04008147.3, filed Apr. 2, 2004, each of which is hereby incorporated by reference." with -- a continuation of U.S. patent application Ser. No. 11/547,011, filed Oct. 2, 2006, which is a National Stage of PCT/EP2005/051490, filed Apr. 1, 2005, which claims priority to EP Application No. 04008147.3, filed Apr. 2, 2004, each of which is hereby incorporated by reference. --

Signed and Sealed this
Ninth Day of July, 2019

Andrei Iancu
*Director of the United States Patent and Trademark Office*